United States Patent
Lian et al.

(10) Patent No.: US 7,603,172 B2
(45) Date of Patent: Oct. 13, 2009

(54) SYSTEM AND METHOD OF USING REGRESSION MODELS TO ESTIMATE VULNERABLE PERIODS FOR HEART STIMULATION PARAMETERS

(75) Inventors: Jie Lian, Beaverton, OR (US); Dirk Muessig, West Linn, OR (US); Volker Lang, West Linn, OR (US)

(73) Assignee: Biotronik CRM Patent AG, Baar (CH)

(*) Notice: Subject to any disclaimer, the term of this patent is extended or adjusted under 35 U.S.C. 154(b) by 376 days.

(21) Appl. No.: 11/560,141

(22) Filed: Nov. 15, 2006

(65) Prior Publication Data

US 2008/0114411 A1   May 15, 2008

(51) Int. Cl.
*A61N 1/362* (2006.01)

(52) U.S. Cl. .................. 607/14; 607/9; 607/15; 607/17; 607/25

(58) Field of Classification Search ............. 607/14, 607/17, 18, 25
See application file for complete search history.

(56) References Cited

U.S. PATENT DOCUMENTS

| | | | | |
|---|---|---|---|---|
| 5,391,189 | A | * | 2/1995 | van Krieken et al. ......... 607/17 |
| 5,697,884 | A | * | 12/1997 | Francischelli et al. ........ 600/17 |
| 2001/0007948 | A1 | | 7/2001 | Stoop et al. |
| 2004/0087843 | A1 | * | 5/2004 | Rice et al. ............... 600/319 |
| 2004/0220631 | A1 | * | 11/2004 | Burnes et al. ............... 607/9 |

FOREIGN PATENT DOCUMENTS

| | | |
|---|---|---|
| EP | 0793979 | 9/1997 |
| EP | 1491234 | 12/2004 |

OTHER PUBLICATIONS

European Search Report dated Jan. 15, 2008.

* cited by examiner

*Primary Examiner*—Carl H Layno
*Assistant Examiner*—Pamela M Bays
(74) *Attorney, Agent, or Firm*—Dalina Law Group, P.C.

(57) ABSTRACT

Heart stimulator that provides for timing a premature stimulation pulse for anti-tachycardia pacing outside the vulnerable phase of a ventricle, to terminate stable ventricular tachycardia while minimizing the risk of accelerating stable ventricular tachycardia into unstable ventricular tachycardia or ventricular fibrillation. RT interval is determined instead of QT interval. Conventional QT interval is defined to end at T wave offset, which is difficult to measure because inherent imprecision in identifying the end of T wave from surface ECG. For safe ATP, such problems may be avoided. Because the VP usually refers to the portion of the T wave near the peak and early downslope (FIG. 3), in order to avoid the VP, only need to determine the peak of T wave, then set an blanking window or safety margin (e.g., 20 ms before to 20 ms after the peak of T wave) during which ATP pulses should not be delivered.

20 Claims, 3 Drawing Sheets

SYSTEM AND METHOD OF USING REGRESSION MODELS TO ESTIMATE VULNERABLE PERIODS FOR HEART STIMULATION PARAMETERS

BACKGROUND OF THE INVENTION

1. Field of the Invention

The invention refers to a heart stimulator for stimulating at least a ventricle of a heart by means of electrical stimulation pulses in an overdrive stimulation mode wherein stimulation pulses to the ventricle are sought to be delivered prior to an intrinsic excitation of said ventricle. The invention particularly refers to implantable cardiac pacemakers and to implantable cardioverter/defibrillators (ICDs).

2. Description of the Related Art

Implantable heart stimulators can be used for treating a variety of heart disorders like bradycardia, tachycardia or fibrillation.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse having strong enough a strength causes an excitation of the myocardium that in turn is followed by a contraction of the respective heart chamber. A stimulation pulse also is called a pace. Similarly, pacing a heart chamber means stimulating a heart chamber by delivery of a stimulation pulse.

In order to be able to sense a contraction of a heart chamber that naturally occurs without artificial stimulation (also called intrinsic contraction), the heart stimulator usually comprises at least one sensing stage that is connected to a sensing electrode on said electrode placed in the heart chamber. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively.

Similarly, common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events $A_S$ (atrial sensed event) or intrinsic ventricular events $V_S$ (ventricular sensed event), respectively.

As known in the art, separate sensing and pacing stages are provided for three-chamber (RA, RV, LV) or four-chamber (RA, LA, RV, LV) pacemakers or ICDs.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited.

Depending upon which chambers of heart are stimulated and which sense events are used different modes of stimulation become available. These modes of stimulation are commonly identified by a three letter code wherein the first letter identifies the chamber or chambers to be stimulated such as V for a ventricle to be stimulated, A for an atrium to be stimulated and D (dual) for both, ventricle and atrium to be stimulated. Similarly, the second letter characterizes the chamber or chambers sensed events may origin from (V: ventricle, A: atrium, D: ventricle and atrium). The third letter characterizes the mode of delivery of stimulation pulses: T=triggered, I=inhibited and D=dual (T+I). A fourth letter "R" may characterize a rate adaptive heart stimulator that comprises an activity sensor or some other means for determining the hemodynamic need of a patient in order to adapt the stimulation rate accordingly.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

By means of a ventricular sensing stage the heart stimulator is able to determine whether the heart undergoes a ventricular tachyarrhythmia that needs to be treated. Typically, a ventricular tachycardia (VT) is treated by way of overdrive pacing the ventricle with a stimulation rate that is higher than the intrinsic ventricular heart rate. Overdrive stimulation requires that the interval between consecutive ventricular stimulation pulses is shorter than an intrinsic (natural) VV-interval between consecutive ventricular excitations. The stimulation interval corresponding to an overdrive stimulation rate is called overdrive interval. The therapy using overdrive stimulation for treating a ventricular tachycardia is called anti tachycardia pacing ATP. ATP shall interrupt a ventricular tachycardia by interrupting a reentry cycle that oftentimes causes the tachycardia. If VT is not treated it may develop into life threatening ventricular fibrillation (VF).

For antitachycardia pacing (ATP), a VVI or a DDI mode of stimulation may be adequate. In such VVI or DDI mode, a ventricular stimulation pulse is not synchronized with a preceding atrial sense event (not "triggered" by an atrial sense event). In the VVI mode no atrial events are sensed nor are atrial stimulation pulses delivered. Only the ventricle is stimulated in a demand mode wherein ventricular stimulation pulses are inhibited if an intrinsic ventricular event is sensed prior to time out of a respective escape interval. In the DDI mode, both, atrium and ventricle, are stimulated in a demand mode wherein atrial or ventricular stimulation pulses are inhibited if an intrinsic atrial or ventricular event is sensed prior to time out of a respective escape interval.

The concept of ATP is based on the observation that VT often involves reentry, which usually has an excitation gap between the leading edge of excitation wavefront and the trail of refractoriness. By delivery a critically timed premature stimulation pulse (or train of stimulation pulses), ATP may pre-excite the excitation gap and disrupt the reentry circle. With improper timing, the ATP may miss the excitation gap and cannot terminate the reentrant rhythm.

Timing of stimulation pulses therefore is crucial. When stimulating a heart with an overdrive stimulation rate, it is attempted to deliver a (premature) stimulation pulse prior to a possible intrinsic excitation and thus render a respective heart chamber refractory so it is not susceptible to any further (natural) excitation during a (natural) refractory period needed by the cells of the myocardium to repolarize and thus become susceptible for further excitation again. However, too early a stimulation pulse would either be ineffective because the myocardium is still refractory (that is not susceptible to intrinsic or stimulated excitation because the myocardium is still depolarized) or, even worse, could meet the vulnerable phase of the myocardium, bearing a high potential risk of inducing a ventricular fibrillation that is worse than tachycardia to be treated. During the vulnerable phase the myocardium has only partially repolarized.

In a heart cycle, an excitation of the myocardium leads to depolarization of the myocardium that causes a contraction of the heart chamber. If the myocardium is fully depolarized it is unsusceptible for further excitation and thus refractory. Thereafter, the myocardium repolarizes and thus relaxes and the heart chamber is expanding again. In a typical electrogram (EGM) depolarization of the ventricle corresponds to an R-wave. The vulnerable phase of the ventricular myocardium coincides with the T-wave.

If the pacing pulses happen to coincide with the vulnerable period (VP), which is defined as a critical time window around the peak of T wave in surface ECG, the ATP are prone to induce fast or unstable VT. This is the well-known "R-on-T" phenomenon.

Despite different ATP algorithms (burst, ramp, scanning, etc), most ICDs are programmed to deliver ATP pulses with slightly shorter cycle length than that of the detected VT, based on predefined cycle percentage or step decrement. So far, there has been no consensus on "optimal" ATP timing parameters. In clinical practice, the setting of ATP timing parameters in ICDs is arbitrary or based on experience. As a result, current ATP algorithms have intrinsic risk of inducing VT/VF, because these algorithms are not designed to prevent the incidence of R-on-T events. In other words, there are intrinsic risks that ATP pulses are delivered during the ventricular VP.

Current ATP algorithms can only effectively terminate about 80 to 95% of spontaneous episodes of slow VT, and is not recommended to treat fast VT or VF. It is also observed that the present ATP algorithms have potential risk (ranging from 2% to nearly 20% likelihood) of accelerating a stable hemodynamically tolerated VT into an unstable VT or VF. Such failed ATP attempts may delay therapy, resulting in syncope, and lead to painful shock therapies.

A premature ventricular stimulation pulse for disrupting a ventricular tachycardia in the course of anti tachycardia pacing is considered safe if it is delivered during a window that is outside the VP. According to this invention, the timing of T wave is estimated from the preceding RR interval based on a programmed QT-RR relationship.

The QT-RR relationship has been extensively investigated during the past decades. It is well known that the QT interval is rate-dependent. In order to compare the QT interval recorded at different heart rates, effort has been made to estimate the heart-rate corrected QT interval (QTc), which relates the QT interval with the RR interval in a predefined mathematical formula, based on statistical regression analysis. Although dozens of QTc formulas have been proposed (linear model, hyperbolic model, parabolic model, etc.), controversial results on optimal regression parameters have been reported.

For the purpose of this disclosure, the following abbreviations are used are used:

TABLE 1

| Abbreviation | Meaning |
|---|---|
| Ap | Atrial pace (stimulation) event |
| As | Atrial sense event |
| A | Any atrial event |
| AVD | AV delay as applied by the pacemaker (in contrast to intrinsic AV delay) |
| ATP | anti tachycardia pacing |
| PVARP | post ventricular atrial refractory period |
| QT | QT interval |
| $QT_c$ | corrected QT interval |
| RR | Peak-to-Peak interval between two consecutive R-waves |
| RT | Peak-to-Peak interval between an R-wave and a T-wave in a same heart cycle |
| RVp | Right ventricular pacing interval for safe ATP |
| Vp | Ventricular pace (stimulation) event |
| Vs | Ventricular sense event |
| V | Any ventricular event |
| VT | Ventricular tachycardia |
| VF | ventricular fibrillation |

BRIEF SUMMARY OF THE INVENTION

It is an object of the invention to provide a heart stimulator that provides a means for timing a premature stimulation pulse for anti tachycardia pacing outside the vulnerable phase of a ventricle, in order to terminate stable ventricular tachycardia while minimizing the risk of accelerating stable ventricular tachycardia into unstable ventricular tachycardia or ventricular fibrillation.

According to the present invention the object of the invention is achieved by a heart stimulator featuring:

a stimulation pulse generator adapted to generate electric stimulation pulses and being connected or being connectable to at least a ventricular stimulation electrode for deliver-ing electric stimulation pulses to at least said ventricle of the heart, a sensing stage connected or being connectable to an electrode for picking up electric potentials inside at least said ventricle of a heart, said sensing stage being adapted to sense an excitation or a contraction of a heart chamber, and a control unit that is connected to said sensing stage and to said stimulation pulse generator and to a memory that contains patient specific data characterizing the time relation between an intrinsic heart rate as characterized by an RR-interval and a QT-interval characterizing the time period from the beginning of a heart cycle to the end of the vulnerable period in that heart cycle.

The control unit is adapted to calculate an antitachycardia pacing (ATP) interval based on a patient specific data stored in said memory such that a premature stimulation pulse is triggered past a vulnerable phase and prior to an intrinsic excitation of the chamber to be stimulated.

Although the following descriptions are given in the context of dual-chamber pacemaker or ICD, it should be understood that the same principle is also applicable to the three-chamber or four-chamber CRT or CRT-D devices.

The invention is based on the idea that the QT-RR relationship could be individually optimized. It was demonstrated that the QT-RR relationship has remarkable intra-subject stability. Previous studies clearly showed that it is feasible to estimate relatively accurate QT interval from the RR intervals, provided that the subject-specific QT-RR relationship is properly established a priori.

According to the invention an RT interval is determined instead of the QT interval. Conventional QT interval is defined to end at T wave offset, which is difficult to measure because there is inherent imprecision in identifying the end of the T wave from the surface ECG. For the purpose of safe ATP, such problems may be avoided. Because the VP usually refers to the portion of the T wave near the peak and early downslope (FIG. 3), in order to avoid the VP, we only need to determine the peak of T wave, then set an associated blanking window or safety margin (e.g., 20 ms before to 20 ms after the peak of T wave) during which ATP pulses should not be delivered. Therefore, it is not necessary to identify the T wave offset for QT interval measurement. Instead, the task becomes much easier to measure the RT interval, i.e., the time interval between peak of R wave and peak of T wave (FIG. 3). Based on the measured RR interval and RT interval data, regression analysis can be performed to determine the RT-RR relationship. Once such a regression model is determined, the boundaries of VP can be estimated given a preset window width.

In a preferred embodiment, the patient is monitored during a calibration period when the RR intervals and RT intervals are measured from surface ECG, or intracardiac electro-gram (IEGM), or the pseudo-ECG estimated from the IEGM. Then statistical regression analysis of the RT-RR relationship is conducted to obtain the patient-specific RT-RR regression model. Different regression models (linear model, hyperbolic model, parabolic model, etc.) with different regression parameters are tested to search for the optimal RT-RR regression model, which is defined to have the lowest residuum between modeled data and measured data. Such statistical regression analysis can be conducted offline in the programming device, and the resulting optimal RT-RR regression model and its parameters are stored as patient specific data into the memory of the heart stimulator. Using this model, for each QRS complex or ventricular depolarisation, its RT interval can be predicted based on preceding RR interval. Therefore, the vulnerable phase VP around the T wave can be properly estimated.

In a preferred embodiment, the calibration and regression analysis of RT-RR relationship is taken for each subject prior to implantation or first use of the heart stimulator, during each follow-up, and every time after change of drug therapy. Such an analysis can be performed based on standard surface ECG obtained during 24-hour Holter recording, or can be obtained with minutes of ECG recording during an treadmill test with predefined exercise protocol that covers certain heart rate range. In another embodiment, if RT-RR calibration data is not available, default ATP timing parameters can be set by using conventional methods (e.g., 85% cycle percentage), or based on generic regression model (e.g., using simple linear model with predefined parameters). However, optimiza-tion of the regression model should be performed whenever the updated RT-RR data are available. To facilitate firmware implementation and reduce computation cost, an RT-RR lookup table can be pre-calculated based on the regression model and downloaded into the memory of the heart stimulator.

Alternatively, the VP zone can be estimated based on the RT-RR plot without regression analysis. For example, for each RR interval or binned RR interval range, the associated VP boundary can be estimated based on the distribution of the corresponding RT intervals. To ensure the safety of ATP without risk of R-on-T event, the ATP pulses should be delivered during a window that is outside the VP while before the next spontaneous ventricular excitation.

The present invention provides heart stimulator providing a means of rational determination of the ATP timing that is individually optimized, so that it is effective in terminating stable VT, meanwhile minimizes the risk of proarrhythmic effect.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
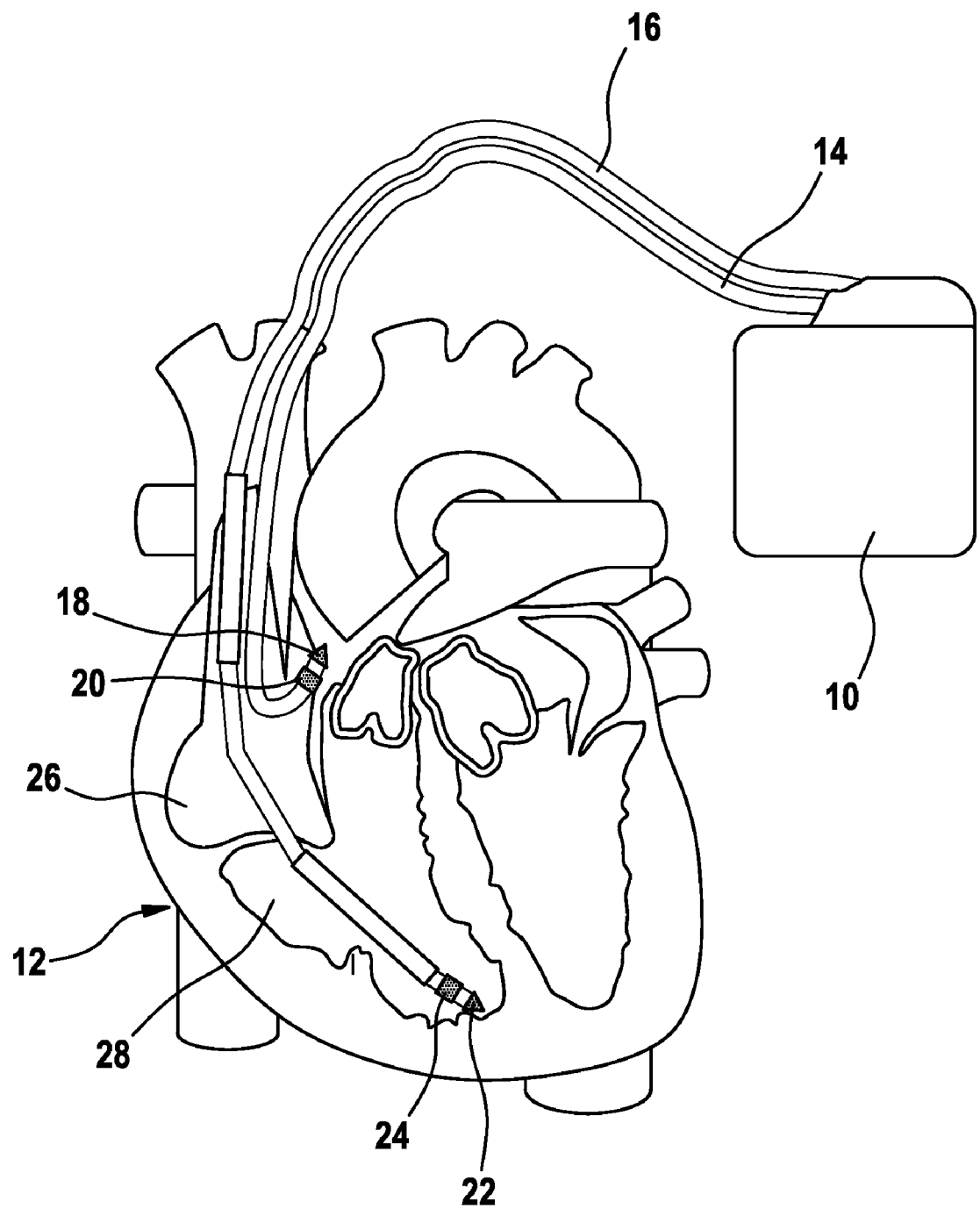
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
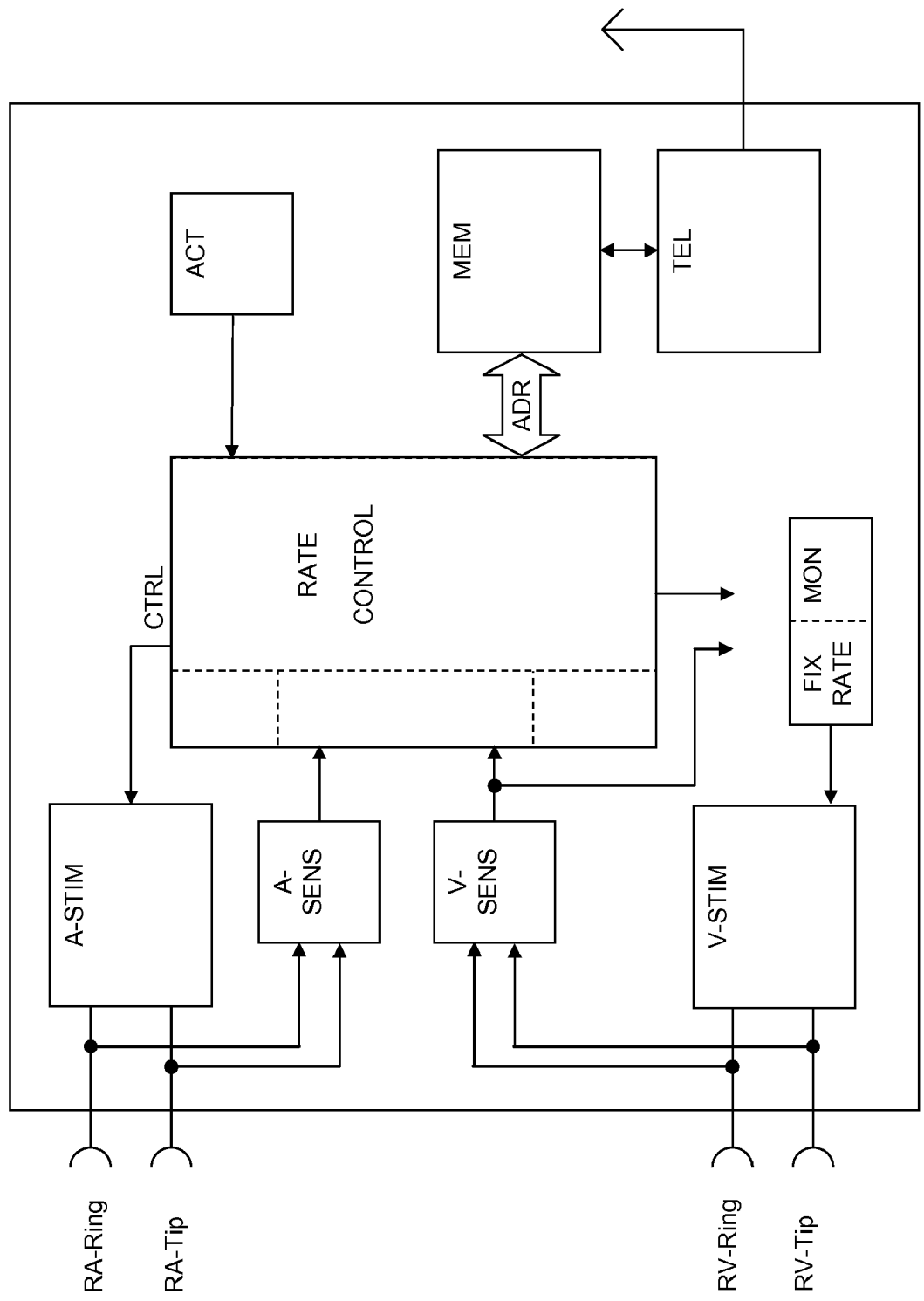
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respec-tive output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atrium are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier V-SENSE.

Controlling the dual chamber pacer 10 is a control unit CTRL that is connected to sense amplifiers A-SENSE and V-SENSE that form respective sensing stages and to stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave representing an intrinsic atrial event or an R-wave representing an intrinsic ventricular event, respectively, is sensed within the heart 12. An As-signal is generated, when the atrial sense amplifier A-SENSE detects a P-wave and a Vs-signal is generated, when the ventricular sense amplifier V-SENSE detects an R-wave.

Control unit CTRL also generates trigger signals that are sent to the atrial stimulation pulse generator A-STIM and the ventricular stimulation pulse generator V-STIM, (via the FIX RATE, MON units), respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or V-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events Ars recorded shortly after delivery of a V-pulses during a preset time interval called post ventricular atrial refractory period (PVARP) are generally recorded but ignored.

Control unit CTRL comprises circuitry for timing ventricular and/or atrial stimulation pulses according to an adequate stimulation rate that can be adapted to a patient's hemodynamic need as pointed out below.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmable stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR or a DDIR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now the operation of pacemaker 10 shall be illustrated.

Control unit CTRL and memory MEM are adapted to calculate an RVp interval for timing of a safe antitachycardia stimulation pulse Vp at the end of the RVp interval beginning with an R-wave (corresponding to a ventricular sense event Vs). Calculation is based on an actual heart rate (RR-interval) that is sensed by means of ventricular sensing stage V-SENSE and on patient specific data stored in memory MEM defining the patient specific relationship between an RR-interval and a QT-interval (or an RT-interval).

In one embodiment, the patient is monitored during a calibration period when the RR intervals and QT intervals are measured from surface ECG, or IEGM, or pseudo-ECG estimated from the IEGM. Then statistical regression analysis of the QT-RR relationship is conducted to obtain the patient-specific RT-RR regression model. Different regression models (linear model, hyperbolic model, parabolic model, etc.) with different regression parameters are tested to search for the optimal QT-RR regression model, which is defined to have the lowest residuum between modeled data and measured data. Such statistical regression analysis can be conducted offline in the programming device, and the resulting optimal QT-RR regression model and its parameters are stored as patient specific data into the memory MEM of the pacemaker 10.

In a preferred embodiment, the calibration and regression analysis of QT-RR relationship is taken for each subject prior to implantation of pacemaker/ICD 10, during each follow-up, and every time after change of drug therapy. Such an analysis can be performed based on standard surface ECG obtained during 24-hour Holter recording, or can be obtained with minutes of ECG recording during an treadmill test with pre-defined exercise protocol that covers certain heart rate range. In another embodiment, if QT-RR calibration data is not available, default ATP timing parameters can be set by using conventional methods (e.g., 85% cycle percentage), or based on generic regression model (e.g., using simple linear model with predefined parameters). However, optimization of the regression model should be performed whenever the updated QT-RR data are available. To facilitate firmware implementation and reduce computation cost, a QT-RR lookup table can be pre-calculated based on the regression model and stored into memory MEM.

Figure 3:
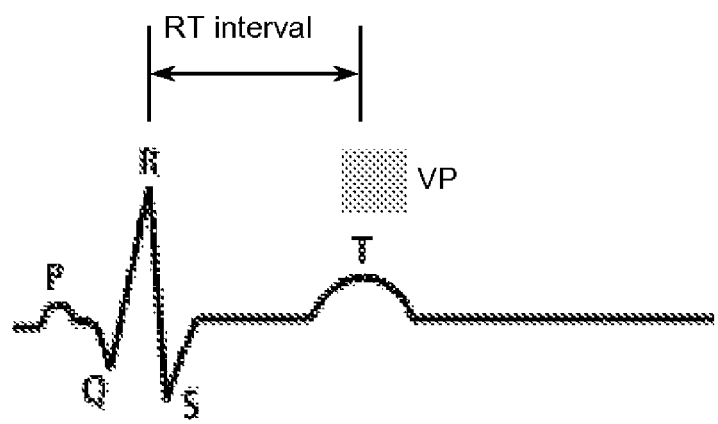
FIG. 3 is an electrocardiogram representing one heart cycle and the vulnerable phase VP.

In another embodiment, instead of using conventional QT interval that is defined to end at T wave offset, which is difficult to measure because there is inherent imprecision in identifying the end of the T wave from the surface ECG, the RT interval which is defined from the peak of an R-wave to the peak of the T-wave is measured. Because the VP usually refers to the portion of the T wave near the peak and early downslope (FIG. 3), in order to avoid the VP, one only needs to determine the peak of T wave, then set an associated blanking window or safety margin (e.g., 20 ms before to 20 ms after the peak of T wave) during which ATP stimulation pulses should not be delivered. Therefore, it is not necessary to identify the T wave offset for QT interval measurement. Instead, the task becomes much easier to measure the RT interval. Based on the measured RR interval and RT interval data, similar regression analysis can be performed to determine the RT-RR relationship. Once such a regression model is determined, the boundaries of VP can be estimated given a preset window width.

Figure 4:
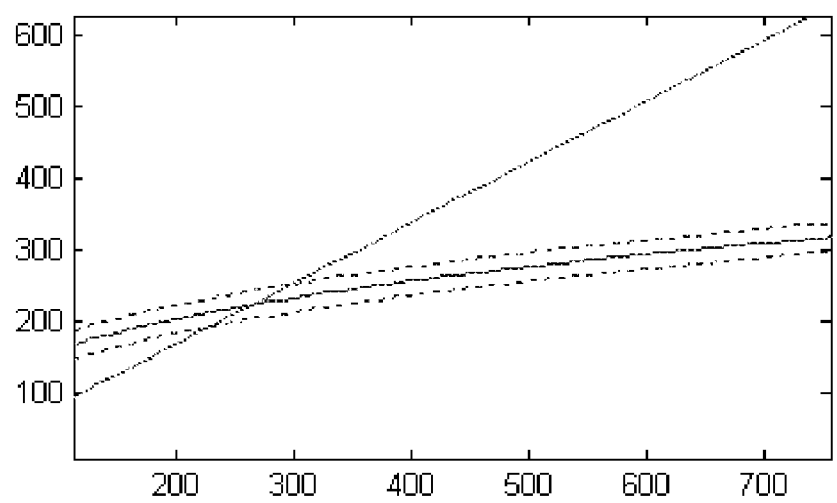
FIG. 4 shows an example of the simulated RT-RR relationship and the estimated VP zone using a parabolic regression model.

Yet in another embodiment, the estimation of the VP zone may be directly estimated from the RT-RR plot, that is, without the computation effort of the regression analysis. More specifically, a 2D scatter graph is obtained by plotting all pairs of (RT, RR) values. For each RR interval (or a binned RR interval range), there is a distribution of the correspond-ing RT intervals, which could be used to define the boundary of the VP for this RR interval (or the binned RR interval range). For example, the upper/lower boundary of the VP for this RR interval (or the binned RR interval range) could be defined as the max/min RT interval, or a programmable +/−percentile (e.g. +/−85%) of the RT interval distribution. By examining the distribution of RT intervals corresponding to each RR interval (or binned RR interval range), a complete VP zone can be defined. FIG. 4 shows an example of the simulated RTpp-RR relationship estimated using a parabolic regression model (QT=$\beta \cdot RR^{\alpha}$ where $\alpha=\frac{1}{3}$, $\beta=0.35$), but with QT being replaced with RT. The VP (from t1 to t2 with respect to the peak of R wave) is estimated as:

$$VP=(t1,t2)=(RT-20\ ms, RT+20\ ms)$$

Alternatively, the lower and upper boundary of VP (t1, t2) may also be estimated using the same regression formula, but changing parameter $\beta$ to $\beta-\delta 1$, and $\beta+\delta 2$, respectively, where $\delta 1$ and $\delta 2$ are small positive constants. In FIG. 4, the solid line surrounded by a pair of dotted lines represents the estimated RT curve, and the dotted lines represent the upper and lower boundary of the VP (t1, t2). The solid line not surrounded by a pair of dotted lines represents the timing based on 85% of the preceding RR cycle length. Clearly, in this simulated case, if the ATP timing parameter is set as 85% of the preceding RR interval (conventional ATP timing method), the pacing pulses will have high probability to coincide with the vulnerable period, particularly if the RR interval is in the range from 230 ms to 300 ms. By avoiding such VP zone, the present ATP timing approach is safer and minimizes the risk of R-on-T events.

Although the QT interval is mainly dependant on heart rate, the effects of other factors such as the autonomic tone and the "lag hysteresis" may also affect the QT interval. According to the present invention, one means to include the "lag hysteresis" into safe ATP timing protocol is by estimating QT (or RT) interval from the weighted average of RR intervals of multiple preceding beats. Such a moving average method can approximately simulate the delayed QT-RR response to sudden heart rate change, thus partially compensate for the "lag hysteresis". It is likely that the QT-RR relationship may exhibit certain circadian pattern, considering varying levels of autonomic modulation, thus corresponding adjustment of regression parameters for day and night may be implemented.

The present invention also provides a means for determining the available time zone for safe triggering of an antitachycardia stimulation (ATP) pulse. In order to safely terminate ventricular tachycardia VT, the ATP pulses should be delivered after the VP while before the next spontaneous ventricular excitation. Such a safe ATP time zone is available if the upper bound of VP is shorter than the subsequent RR interval. However, when the heart rate is too high, such a time gap may not be available because the subsequent R wave may occur during or even earlier than the VP (e.g., when RR interval is shorter than 220 ms in FIG. 4). From this point of view, the patient-specific RT-RR regression model can be used to predict the availability of safe ATP time zone. Because of the inter-subject variability, the relationship between VP and RR interval may vary among subjects. Therefore, the time zone for safe ATP may still be available for very short RR interval in some patients, whereas it may not be available for relatively long RR interval in other patients.

The concept of "safe timing" disclosed in this invention is not limited to ATP therapy. For example, if the VP can be properly estimated from preceding RR interval, then the ventricular pacing should be timed after the VP for other ventricular pacing protocols, such as ventricular rate smoothing and biventricular pacing, to reduce the risk of R-on-T events. Similarly, a cardiac contractility modulation therapy for heart failure treatment requires non-exciting pacing during the absolute refractory period, which is shortly after the QRS complex, and should be timed well-before the onset of VP. Furthermore, the concept of "safe timing" may also be applied to shock therapy by means of an implantable cardioverter/defibrillator (ICD). It was suggested that the ventricular defibrillation threshold has probabilistic nature, in that the shock outcome is a function of the amount of myocardium in its VP. By delivery cardioversion or shock during a time window not overlying with the VP, lower energy discharge and higher success rate to terminate the life-threatening VT/VF may be achieved.

What is claimed is:

1. A heart stimulator for stimulating at least a ventricle of a heart comprising:
    a stimulation pulse generator adapted to generate electric stimulation pulses and connected or connectable to at least a ventricular stimulation electrode configured to deliver electric stimulation pulses to at least said ventricle of said heart;
    a sensing stage connected or connectable to an electrode configured to pick up electric potentials inside at least said ventricle of said heart, said sensing stage adapted to sense an excitation or a contraction of a heart chamber;
    a control unit, which is connected to said sensing stage and to said stimulation pulse generator and which is adapted to trigger said stimulation pulse generator in a safe antitachycardia pacing time zone before a start or after an end of a vulnerable period in a heart cycle and prior to an expected intrinsic excitation of said heart chamber to be stimulated when said heart stimulator is in an anti-tachycardia pacing mode of operation;
    memory connected to said control unit that contains patient specific data that characterizes a time relation between an intrinsic heart rate as characterized by an RR-interval and a QT-interval characterized by a time period from a beginning of the heart cycle to an end of the vulnerable period in that heart cycle wherein said patient specific data comprises an RT-RR or a QT-RR regression model to estimate the vulnerable period at high heart rates where no corresponding RT-RR or QT-RR calibration data exists at said high heart rates; and, wherein said control unit is adapted to calculate an RVp interval based on a patient specific relation of a heart rate and said QT-interval such that a stimulation pulse is triggered shortly before said start or after said end of said vulnerable period for an actual heart rate.

2. The heart stimulator according to claim 1, wherein said patient specific data that characterizes said time relation between said RR-interval and said QT-interval is based on measurement of a plurality of RT intervals that span from a peak of an R-wave to a peak of a T-wave in a same heart cycle and that are measured for different intrinsic heart rates of said specific patient that said heart stimulator is set up for.

3. The heart stimulator according to claim 2, wherein said memory contains said RT-RR regression model formed with statistical regression analysis of a QT-RR relationship.

4. The heart stimulator according to claim 2, wherein said memory contains a pre-calculated RT-RR or QT-RR lookup table comprising RR-interval values and RT or QT interval values corresponding to said RR interval values.

5. The heart stimulator according to claim 4, wherein said control unit is adapted to calculate an actual RT interval based on said pre-calculated RT-RR lookup table based on interpolation of RT interval values stored in said memory.

6. The heart stimulator according claim 1, wherein said control unit is adapted to calculate an actual RT interval based on said RT-RR regression model and an actual RR-interval.

7. The heart stimulator according to claim 6 wherein said control unit is adapted to calculate the RVp interval that starts with a sensed R-wave and ends with a trigger of a premature ventricular stimulation pulse based on a calculated actual RT-interval, wherein said RVp interval comprises said RT interval and a safety margin.

8. The heart stimulator according to claim 7, wherein said control unit is adapted to calculate said RVp interval through multiplication of said calculated actual RT interval with a factor between 1.1 and 1.3.

9. The heart stimulator according to claim 7, wherein said control unit is adapted to calculate said RVp interval through addition of said calculated actual RT interval with a time period between 20 and 50 ms.

10. The heart stimulator according to claim 1, wherein said patient specific data is calculated based on a generic regression model when RT-RR calibration data is not available.

11. The heart stimulator according to claim 1, wherein said control unit is further adapted to predict availability of the safe anti-tachycardia pacing time zone based on said patient specific data.

12. A method of setting up a heart stimulator comprising:
measuring an RT interval from a peak of an R-wave to a peak of a T-wave within a heart cycle;
measuring an RR interval from said peak of said R-wave to a peak of a next R-wave for said heart cycle;
determining an interval pair comprising said RT interval and said RR interval belonging together;
determining a plurality of interval pairs for different heart rates by repeating said steps of measuring said RT interval and measuring said RR-interval for different states of physical or mental load of a patient;
determining a functional relationship between said plurality of interval pairs thus determined in order to enable calculation of an RT interval for a given RR interval, said functional relationship characterized by patient specific data that comprises an RT-RR or a QT-RR regression model to estimate a vulnerable period at high heart rates that are higher than said different heart rates and where no corresponding RT-RR or QT-RR calibration data exists at said high heart rates; and,
storing said patient specific data in memory of said heart stimulator.

13. The method according to claim 12, further comprising determining said functional relationship by regression analysis and calculating an RT-RR or QT-RR regression model.

14. The method according to claim 13, further comprising storing said RT-RR regression model into said memory after performing statistical regression analysis of a QT-RR relationship.

15. The method according to claim 13, further comprising pre-calculating an RT-RR lookup table based on said RT-RR regression model and storing said RT-RR lookup table into said memory.

16. The method according to claim 12, further comprising determining said functional relationship by estimation from an RT-RR plot.

17. The method according to claim 12, further comprising estimating said RT interval from a weighted average of multiple preceding RR intervals to account for QT-RR lag hysteresis.

18. The method according to claim 12, wherein said determining of said functional relationship between said plurality of interval pairs is carried out separately for different periods in a circadian cycle.

19. The method according to claim 12, further comprising calculating said patient specific data based on a generic regression model when RT-RR calibration data is not available.

20. The method according to claim 12, further comprising predicting availability of a safe anti-tachycardia pacing time zone based on said patient specific data.

* * * * *